(12) United States Patent
Goettel et al.

(10) Patent No.: US 7,462,204 B2
(45) Date of Patent: Dec. 9, 2008

(54) CATIONIC DIAMINOPYRAZOLES, A PROCESS FOR PRODUCING THEM AND COLORANTS CONTAINING THESE COMPOUNDS

(75) Inventors: Otto Goettel, Marly (CH); Andre Hayoz, Senedes (CH); Emmanuel Morand, Villars-sur-Glane (CH)

(73) Assignee: Wella AG, Darmstadt (DE)

( * ) Notice: Subject to any disclaimer, the term of this patent is extended or adjusted under 35 U.S.C. 154(b) by 226 days.

(21) Appl. No.: 10/576,090

(22) PCT Filed: Sep. 2, 2004

(86) PCT No.: PCT/EP2004/009795

§ 371 (c)(1),
(2), (4) Date: Apr. 18, 2006

(87) PCT Pub. No.: WO2005/051918

PCT Pub. Date: Jun. 9, 2005

(65) Prior Publication Data

US 2007/0056120 A1      Mar. 15, 2007

(30) Foreign Application Priority Data

Nov. 21, 2003   (DE)   ................... 10354584

(51) Int. Cl.
*A61Q 5/10* (2006.01)
(52) U.S. Cl. ............ 8/405; 8/406; 8/409; 8/410; 8/421; 8/423; 8/568
(58) Field of Classification Search .......... 8/405, 8/406, 409, 410, 421, 423, 568
See application file for complete search history.

(56) References Cited

U.S. PATENT DOCUMENTS 6,660,046 B1 *   12/2003   Terranova et al. .............. 8/405

FOREIGN PATENT DOCUMENTS

| WO | 97/42173 | 11/1997 |
| WO | 00/43367 | 7/2000 |
| WO | WO 00/43367 | * 7/2000 |
| WO | 02/46165 | 6/2002 |

OTHER PUBLICATIONS

STIC Search Report dated Dec. 4, 2007.*

* cited by examiner

*Primary Examiner*—Eisa B Elhilo
(74) *Attorney, Agent, or Firm*—Michael J. Striker

(57) ABSTRACT

Novel cationic 4,5-diaminopyrazole derivatives of general formula (I)

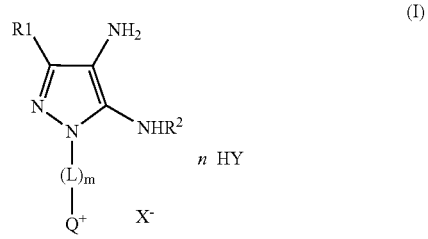

the colorants for keratin fibers containing these compounds and a process for producing the compounds of formula (I).

6 Claims, No Drawings

CATIONIC DIAMINOPYRAZOLES, A PROCESS FOR PRODUCING THEM AND COLORANTS CONTAINING THESE COMPOUNDS

CROSS-REFERENCE TO RELATED APPLICATIONS

This application claims priority under 35 U.S.C. 119(a)-(d) to German Patent Application Number DE 103 54 584.0, filed Nov. 21, 2003.

BACKGROUND OF THE INVENTION:

1. Field of the Invention

The present application has for an object novel cationic 4,5-diaminopyrazoles, a process for producing them and colorants containing these compounds.

2. Description of Related Art

Oxidation dyes have attained substantial cosmetic significance in the field of conventional hair dyeing. The color is created by reaction of certain developers and couplers in the presence of an oxidant. Besides the creation of color effects, very high requirements are placed on oxidation dyes that are intended for the treatment of human hair. On the one hand, the dyes must be harmless from a toxicological and dermatological point of view and they must not be sensitizing. Moreover, it must be possible, by a combination of suitable developers and couplers, to produce a wide range of different color nuances. Furthermore, the hair colorations produced are required to have good wash fastness, light fastness, perspiration resistance, resistance to permanent wave treatments, acid resistance, base resistance and abrasion resistance. At any rate, such hair colorations must remain stable for at least four to six week under normal everyday conditions.

In the past, 4-aminophenol has been the primary developer used to cover the important red range. Because of concerns about the physiological compatibility of this substance, derivatives of pyridine and pyrimidine have also been used, but they were not satisfactory from a coloring standpoint. 4,5-Diaminopyrazoles and 4,5-diaminopyrazoles substituted in the 3-position have also been used in place of 4-aminophenol. Moreover, it is known from WO 00/43367 to use cationic pyrazole derivatives of a broad general formula in hair colorants. Most of the compounds referred to in WO 00/43367, however, cannot be prepared by processes presented therein and thus are not available.

Whereas most oxidation dyes show hardly any weaknesses on undamaged hair, they can cause pronounced differences on damaged hair. The hairdresser thus knows from everyday practice that dyes are not uniformly taken up by the hair to be dyed. Whereas, as a rule, the hair roots are intact, with the passage of time the hair tips show damage due to weathering effects, frequent washing and combing, damage that gradually increases from the hair roots to the hair tips. Hence, when such hair is dyed, nonuniform coloring can result because of the nonuniform condition of the hair between the roots and the tips. Another problem lies in the fact that when dyed hair is washed, the dyes are more strongly washed out from the more strongly damaged parts of the hair than from undamaged parts, depending on the degree of hair damage, which after a few washings can gradually become more evident.

To cover the red range in particular, the need continued to exist for suitable dyes capable of being taken up readily and uniformly and of giving colorations with improved stability against shampooing on a wide range of hair qualities, particularly on hair damaged by permanent waving or bleaching.

We have now found that certain cationic pyrazoles meet the afore-said objective in outstanding fashion.

BRIEF SUMMARY OF THE INVENTION

Hence, the object of the present invention are novel cationic 4,5-diaminopyrazole derivatives of general formula (I)

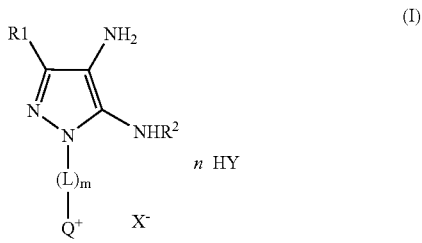

wherein

R1 denotes hydrogen, a straight-chain or branched $(C_1-C_6)$-alkyl group, a $(C_1-C_4)$-hydroxyalkyl group, a $(C_1-C_4)$-aminoalkyl group, a $(C_1-C_8)$-alkylamino group, a $di(C_1-C_8)$-alkylamino group, a $(C_1-C_4)$-alkylamino-$(C_1-C_4)$-alkyl group or a $di(C_1-C_4)$-alkylamino-$(C_1-C_4)$-alkyl group, a benzyl group, an aryl group or a heteroaryl group;

R2 denotes hydrogen, a $(C_1-C_6)$-alkyl group, a $(C_2-C_4)$-hydroxyalkyl group, a $(C_3-C_6)$-polyhydroxyalkyl group, an alkoxyalkyl group with 2 to 6 carbon atoms or a benzyl group;

L denotes a bridging group between the pyrazole ring and the quaternary group and consists of a phenylene diradical or a $(C_1-C_2)$-alkylene diradical;

$Q^+$ stands for a saturated cationic group of formula (II) or an unsaturated cationic group of formula (III) to (V) or for a benzoaromatic analog thereof of formula (VI) to (VIII)

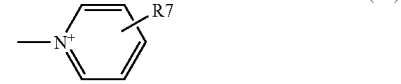

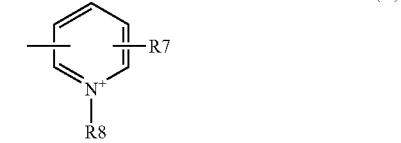

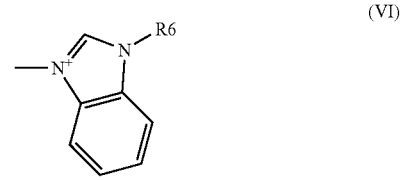

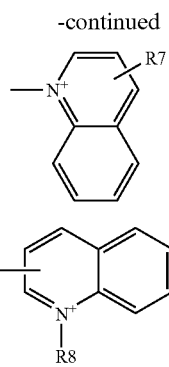

(VII)

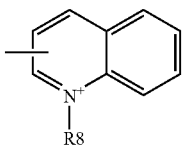

(VIII)

wherein
R3 to R5 can be equal or different and independently of each other denote a straight-chain or branched $(C_1-C_6)$-alkyl group, a $(C_2-C_4)$-hydroxyalkyl group, $(C_3-C_6)$-dihydroxyalkyl group, a $(C_3-C_6)$-polyhydroxyalkyl group or a $(C_1-C_6)$-alkoxy-$(C_1-C_4)$-alkyl group; or two of the R3 to R5 groups together with the nitrogen atom to which they are linked forming a five-membered or six-membered heterocycle optionally containing one or more other heteroatoms (for example O, N, S) and other substituents [for example F, Cl, Br, I, OH, $NH_2$ or a straight-chain or branched $(C_1-C_6)$-alkyl group, a straight-chain or branched $(C_1-C_6)$-alkoxy group, a $(C_1-C_6)$-alkoxy-$(C_1-C_4)$-alkyl group or a hydroxyethyl group];

R6 denotes a straight-chain or branched $(C_1-C_8)$-alkyl group, an allyl group, a vinyl group, a hydroxyethyl group or a benzyl group;

R7 stands for hydrogen, a straight-chain or branched $(C_1-C_9)$-alkyl group, an amino group, a mono-$(C_1-C_6)$-alkylamino group, a di$(C_1-C_6)$-alkylamino group or a pyrrolidino group;

R8 stands for a straight-chain or branched $(C_1-C_8)$-alkyl group, an allyl group, a vinyl group, a hydroxyethyl group, a dihydroxypropyl group or a benzyl group, and $X^-$ denotes a monovalent or polyvalent anion, particularly a chloride, bromide, iodide, alkylsulfate, arylsulfonate, hydrogen sulfate, sulfate, phosphate, acetate or tartrate ion;

HY stands for an inorganic or organic acid;
m is equal to 0 or 1, and
n has a value between 0 and 2.

Preferred are compounds of general formula (I) wherein
R1 denotes hydrogen, a methyl group or a phenyl group;
R2 denotes hydrogen or a methyl group;
R3 to R5 can be equal or different and independently of each other denote a methyl group, ethyl group or hydroxyethyl group; or two of the R3 to R5 groups together with the nitrogen atom to which they are linked forming a pyrrolidino group, morpholino group or N-methylpiperazino group;
R6 stands for a methyl group or a hydroxyethyl group;
R7 stands for hydrogen, a methyl group, p-dimethylamino group or p-pyrrolidino group;
R8 denotes a methyl group, ethyl group or hydroxyethyl group;
$X^-$ denotes a chloride, bromide, methylsulfate, toluenesulfonate, sulfate, phosphate, acetate or tartrate anion;
L denotes a $(C_1-C_2)$-alkylene diradical and m is equal to 1;
HY stands for hydrochloric acid, sulfuric acid, phosphoric acid, acetic acid or tartaric acid, and
n has a value between 0 and 2.

DETAILED DESCRIPTION OF THE INVENTION

Because of the high sensitivity of the compounds of formula (I) to oxidation, it is advantageous for purposes of better handling to isolate them not as the free bases but preferably as their acid adducts. The salts thus obtained are virtually insensitive to air oxidation. Particularly preferred compounds of formula (I) are:

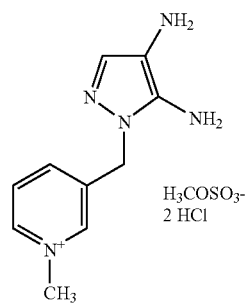

(I-a)

3-[(4,5-diamino-1H-pyrazol-1-yl)methyl]-1-methylpyridinium methylsulfate dihydrochloride

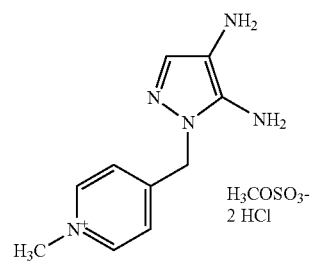

(I-b)

4-[(4,5-diamino-1H-pyrazol-1-yl)methyl]-1-methylpyridinium methylsulfate dihydrochloride

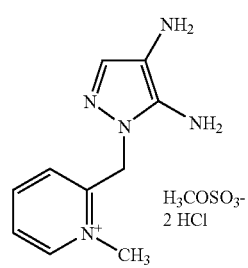

(I-c)

2-[(4,5-diamino-1H-pyrazol-1-yl)methyl]-1-methylpyridinium methylsulfate dihydrochloride

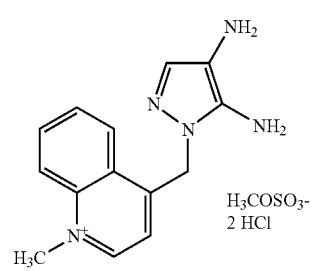

(I-d)

4-[(4,5-diamino-1H-pyrazol-1-yl)methyl]-1-methylquinolinium methylsulfate dihydrochloride

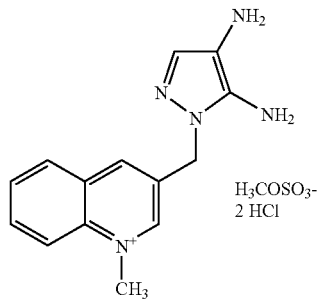
(I-e)

3-[(4,5-diamino-1H-pyrazol-1-yl)methyl]-1-methylquinolinium methylsulfate dihydrochloride

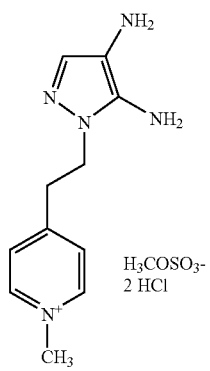
(I-f)

4-[2-(4,5-diamino-1H-pyrazol-1-yl)ethyl]-1-methylpyridinium methylsulfate dihydrochloride

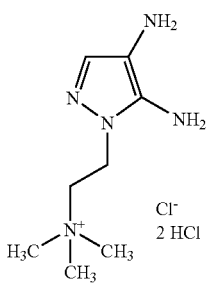
(I-g)

2-(4,5-diamino-1H-pyrazol-1-yl)-N,N,N-trimethylethanaminium chloride dihydrochloride

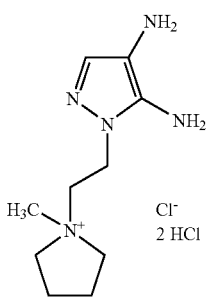
(I-h)

1-[2-(4,5-diamino-1H-pyrazol-1-yl)ethyl]-1-methylpyrrolidinium chloride dihydrochloride

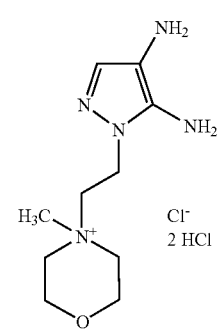
(I-i)

4-[2-(4,5-diamino-1H-pyrazol-1-yl)ethyl]-4-methylmorpholin-4-ium chloride dihydrochloride

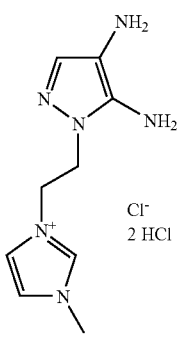
(I-k)

3-[2-(4,5-diamino-1H-pyrazol-1-yl)ethyl]-1-methyl-1H-imidazol-3-ium chloride dihydrochloride The compounds of formula (I) are eminently suited as dye precursors in oxidative systems for coloring keratin fibers. Although the compounds of formula (I) are particularly well suited for coloring keratin fibers, for example wool, silk or hair—and particularly human hair—it is in principle also possible to color with these compounds other natural or synthetic fibers, for example cotton or nylon 66.

Another object of the present invention is therefore an agent for oxidative coloring of keratin fibers—particularly hair—which is characterized in that it contains at least one cationic 4,5-diaminopyrazole of general formula (I) or a salt thereof with an organic or inorganic acid.

The 4,5-diaminopyrazole of formula (I) is contained in the colorant of the invention in an amount from about 0.005 to 20 weight percent, an amount from about 0.01 to 10 weight percent and particularly from 0.1 to 6 weight percent being preferred.

The compounds of formula (I) can be used alone or in combination with other developers and/or couplers that are commonly employed in oxidative coloring systems for coloring fiber materials.

Suitable couplers are, in particular: N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino-1,5-dimethoxybenzene, 2,3-diamino-6- methoxypyridine, 3-amino-6-methoxy-2-(methylamino) pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1-(3-hydroxypropoxy)benzene, 2,4-diamino-1-(3-methoxypropoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di (2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5[(2-hydroxyethyl)amino]-2-methylphenol, 3[(2-hydroxyethyl)amino]-phenol, 3-[(2-methoxyethyl)amino]phenol, 5-amino-2-ethylphenol, 2-(4-amino-2-hydroxyphenoxy) ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 1,3-dihydroxy-2,4-dimethylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 4-hydroxyindole, 5-hydroxyindole, 6-hydroxyindole, 7-hydroxyindole and 2,3-indolinedione or the salts thereof.

To obtain near-natural shades and trendy red shades, it is particularly advantageous to use compounds of formula (I) in combination with additional developers. Suitable developers are p-phenylenediamines, p-aminophenols and other 4,5-diaminopyrazoles or the salts thereof.

Particularly suitable are the following developers: 1,4-diaminobenzene (p-phenylenediamine), 1,4-diamino-2-methylbenzene (p-toluylenediamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylaminoaniline, 4-[di(2-hydroxyethyl)amino]aniline, 4-[(2-methoxyethyl)amino]aniline, 4-[(3-hydroxypropyl)amino] aniline, 1,4-diamino-2-(2-hydroxyethyl)benzene, 1,4-diamino-2-(1-hydroxyethyl)benzene, 1,4-diamino-2-(1-methylethyl)benzene, 3-bis-[(4-aminophenyl)-(2-hydroxyethyl)-amino]-2-propanol, 1,8-bis(2,5-diaminophenoxy)-3,6-dioxaoctane, 4-aminophenol, 4-amino-3-methylphenol, 4-methylaminophenol, 4-amino-2-(aminomethyl)phenol, 4-amino-2-[(2-hydroxyethyl) amino]methylphenol, 4-amino-2-(methoxymethyl)phenol, 4-amino-2-(2-hydroxyethyl)phenol, 5-aminosalicylic acid, 2,5-diaminopyridine, 2,4,5,6-tetraminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]4,5-diamino-1H-pyrazole, 4,5-diamino-1-methyl-1H-pyrazole, 4,5-diamino-3-methyl-1-phenyl-1H-pyrazole, 4,5-diamino-1-(2-hydroxyethyl)-3-methyl-1H-pyrazole, 2-aminophenol, 2-amino-6-methylphenol and 2-amino-5-methylphenol or the salts thereof.

The afore-said developers and couplers are contained in the agent of the invention in a total amount of about 0.01 to 20 weight percent and preferably about 0.2 to 6 weight percent each.

Naturally, the compounds of formula (I) can also be used in combination with common direct anionic, cationic, amphoteric or nonionic dyes. Among the preferred anionic dyes are, for example: disodium 6-hydroxy-5[(4-sulfophenyl)azo]-2-naphthalenesulfonate (Cl 15985; Food Yellow No. 3; FD&C Yellow No. 6), disodium 2,4-dinitro-1-naphthol-7-sulfonate (Cl 10316; Acid Yellow No. 1; Food Yellow No. 1), 2-(indan-1,3-dion-2-yl)quinoline-x,x-sulfonic acid (mixture of mono- and disulfonic acid) (Cl 47005; D&C Yellow No. 10; Food Yellow No. 13, Acid Yellow No. 3), trisodium 5-hydroxy-1-(4-sulfophenyl)-4-[(4-sulfophenyl)azo]pyrazole-3-carboxylate (Cl 19140; Food Yellow No. 4; Acid Yellow No. 23), 9-(2-carboxyphenyl)-6-hydroxy-3H-xanthen-3-one (Cl 45350; Acid Yellow No. 73; D&C Yellow No. 8), sodium 5-[(2,4-dinitrophenyl)amino]-2-phenylaminobenzenesulfonate (Cl 10385; Acid Orange No. 3), monosodium 4-[(2, 4-dihydroxyphenyl)azo]benzenesulfonate (Cl 14270; Acid Orange No. 6), sodium 4-[(2-hydroxynaphth-1-yl)azo]benzenesulfonate (Cl 15510; Acid Orange No. 7), sodium 4-[(2, 4-dihydroxy-3-[(2,4-dimethylphenyl)azo]phenyl)azo]benzenesulfonate (Cl 20170; Acid Orange No. 24), disodium 4-hydroxy-3-[(4-sulfonaphth-1-yl)azo]-1-naphthalenesulfonate (Cl 14720; Acid Red No. 14), trisodium 6-hydroxy-5-[(4-sulfonaphth-1-yl)azo]-2,4-naphthalenedisulfonate (Cl 16255; Ponceau 4R; Acid Red No. 18), trisodium 3-hydroxy-4-[(4-sulfonaphth-1-yl)azo]-2,7-naphthalenedisulfonate (Cl 16185; Acid Red No. 27; disodium 8-amino-1-hydroxy-2-(phenylazo)-3,6-naphthalenedisulfonate (Cl 17200; Acid Red No. 33), disodium 5-(acetylamino)-4-hydroxy-3-[(2-methylphenyl)azo]-2,7-naphthalenedisulfonate (Cl 18065; Acid Red No. 35), disodium 2-(3-hydroxy-2,4,5,7-tetraiododibenzopyran-6-on-9-yl)benzoate (Cl 45430; Acid Red No. 51), N-[6-(diethylamino)-9-(2,4-disulfophenyl)-3H-xanthen-3-ylidene]-N-ethylethanaminium hydroxide, inner salt, sodium salt (Cl 45100; Acid Red No. 52), disodium 8-{[(4-phenylazo)phenyl]azo}-7-naphthol-1,3-disulfonate (Cl 27290; Acid Red No. 73), 2',4',5',7'-tetrabromo-3',6'-dihydroxyspiro[isobenzofuran-1(3H), 9'-[9H]-xanthen]-3-one disodium salt (Cl 45380; Acid Red No. 87), 2',4',5',7'-tetrabromo-4,5,6,7-tetrachloro-3',6'-dihydroxyspiro{isobenzofuran-1(3H), 9'[9H]xanthen}3-one disodium salt (Cl 45410; Acid Red No. 92), 3',6'-dihydroxy-4',5'-diiodospiro[isobenzofuran-1(3H), 9'(9H)-xanthen)-3-one disodium salt (Cl 45410; Acid Red No. 92), 3',6'-dihydroxy-4',5'-diiodospiro[isobenzofuran-1(3H), 9'(9H)-xanthen]-3-one disodium salt (Cl 45425; Acid Red No. 95), (2-sulfophenyl)di[4-(ethyl((4-sulfophenyl)methyl)amino) phenyl]carbenium disodium salt, betaine (Cl 42090; Acid Blue No. 9; FD&C Blue No. 1), 1,4-bis[(2-sulfo-4-methylphenyl)amino]-9,10-anthraquinone disodium salt (Cl 61570; Acid Green No. 25), bis[4-(dimethylamino)phenyl]-(3,7-disulfo-2-hydroxynaphth-1-yl)carbenium inner salt, monosodium salt (Cl 44090; Food Green No. 4; Acid Green No. 50), bis[4-(diethylamino)phenyl](2,4-disulfophenyl)carbenium inner salt, sodium salt (2:1) (Cl 42045; Food Blue No. 3; Acid Blue No. 1), bis[4-diethylamino)phenyl](5-hydroxy-2,4-disulfophenyl)carbenium inner salt, calcium salt (2:1) (Cl 42051; Acid Blue No. 3), sodium 1-amino-4-(cyclohexylamino)-9,10-anthraquinone-2-sulfonate (Cl 62045; Acid Blue No. 62), disodium 2-(1,3-dihydro-3-keto-5-sulfo-2H-indol-2-ylidene)-2,3-dihydro-3-keto-1H-indol-5-sulfonate (Cl 73015; Acid Blue No. 74), 9-(2-carboxyphenyl)-3-[(2-methylphenyl)amino]-6-[(2-methyl-4-sulfophenyl)amino]xanthylium inner salt monosodium salt (Cl 45190; Acid Violet No. 9), 1-hydroxy-4-[(4-methyl-2-sulfophenyl)amino]-9,10-anthraquinone sodium salt (Cl 60730; D&C Violet No 2; Acid Violet No. 43), bis{3-nitro-4-[(4-phenylamino)-3-sulfophenylamino]phenyl}sulfone (Cl 10410; Acid Brown No. 13), disodium 5-amino-4-hydroxy-6-[(4-nitrophenyl)azo]-3-(phenylazo)-2,7-naphthalenedisulfonate (Cl 20470; Acid Black No. 1), 3-hydroxy-4-[(2-hydroxynaphth-1-yl)azo]-7-nitro-1-naphthalenesulfonic acid chromium complex (3:2) (Cl 15711; Acid Black No. 52), disodium 3-[(2,4-dimethyl-5-sulfophenyl)azo]4-hydroxy-1-naphthalenesulfonate (Cl 14700; Food Red No. 1; Ponceau SX; FD&C Red No. 4), tetrasodium 4-(acetylamino)-5-hydroxy-6-[(7-sulfo-4-[(4-sulfophenyl)azo]-naphth-1-yl)azo]-1,7-naphthalenedisulfonate (Cl 28440; Food Black No. 1) and sodium 3-hydroxy-4-(3-methyl-5-keto-1-phenyl-4,5-di-hydro-1H-pyrazol-4-ylazo)naphthalene-1-sulfonate chromium complex (Acid Red No. 195).

Preferred cationic dyes include, for example: 9-(dimethylamino)benzo[a]phenoxazin-7-ium chloride (Cl 51175; Basic Blue No. 6), di[4-(diethylamino)phenyl][4-(ethylamino)naphthyl]carbenium chloride (Cl 42595; Basic Blue No. 7), 3,7-di(dimethylamino)phenothiazin-5-ium chloride (Cl 52015; Basic Blue No. 9), di[4-(dimethylamino)phenyl][4-phenylamino)naphthyl]carbenium chloride (Cl 44045; Basic Blue No. 26), 2-{[4-(ethyl(2-hydroxyethyl)amino)phenyl]azo}-6-methoxy-3-methylbenzothiazolium methylsulfate (Cl 11154; Basic Blue No. 41), 8-amino-2-bromo-5-hydroxy-4-imino-6-{[3-(trimethylammonio)phenyl]amino}-1(4H)-naphthalenone chloride (Cl 56059; Basic Blue No. 99), bis[4-(dimethylamino)phenyl][4-(methylamino)phenyl]carbenium chloride (Cl 42535; Basic Violet No. 1), tris(4-amino-3-methylphenyl)carbenium chloride (Cl 42520; Basic Violet No. 2), tris[4-(dimethylamino)phenyl]carbenium chloride (Cl 42555; Basic Violet No. 3), 2-[3,6-(diethylamino)dibenzopyranium-9-yl]benzoyl chloride (Cl 45170; Basic Violet No. 10), di(4-aminophenyl)(4-amino-3-methylphenyl)carbenium chloride (Cl 42510; Basic Violet No. 14), 1,3-bis-[(2,4-diamino-5-methylphenyl)azo]-3-methylbenzene (Cl 21010; Basic Brown No. 4), 1-[(4-aminophenyl)azo]-7-(trimethylammonio)-2-naphthol chloride (Cl 12250; Basic Brown No. 16), 1-[(4-amino-2-nitrophenyl)azo]-7-(trimethylammonio)-2-naphthol chloride (Cl 12251; Basic Brown No. 17), 1-[(4-amino-2-nitrophenyl)azo]-7-(trimethylammonio)-2-naphthol chloride (Cl 12251; Basic Brown No. 17) [sic], 3,7-diamino-2,8-dimethyl-5-phenylphenazinium chloride (Cl 50240; Basic Red No. 2), 1,4-dimethyl-5-{[4-(dimethylamino)phenyl]azo}-1,2,4-triazolium chloride (Cl 11055; Basic Red No. 22), 2-hydroxy-1-[(2-methoxyphenyl)azo]-7-(trimethylammonio)naphthalene chloride (Cl 12245; Basic Red No. 76), 2-{2-[(2,4-dimethoxyphenyl)amino]ethenyl}-1,3,3-trimethyl-3H-indol-1-ium chloride (Cl 48055; Basic Yellow No. 11), 3-methyl-1-phenyl-4-{[3-(trimethylammonio)-phenyl]azo}pyrazol-5-one chloride (Cl 12719; Basic Yellow No. 57 and bis[4-(diethylamino)-phenyl]phenylcarbenium hydrogen sulfate (1:1) (Cl 42040; Basic Green No. 1).

Suitable nonionic dyes, particularly for improving color balancing and for producing special color nuances are, for example: 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[2-hydroxyethyl)amino]-2-nitrobenzene, (HC Yellow No. 2), 2-[(hydroxyethyl)amino]-1-methoxy-5-nitrobenzene, 2-amino-3-nitrophenol, 1-(2-hydroxyethoxy)-3-methyl-amino-4-nitrobenzene, 2,3-dihydroxypropoxy)-3-methylamino-4-nitrobenzene, 2-[(2-hydroxyethyl)-amino]-5-nitrophenol (HC Yellow No. 11), 3-[(2-aminoethyl)amino]-1-methoxy-4-nitrobenzene hydrochloride (HC Yellow No. 9), 1-[(2-(ureidoethyl)amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1-amino-4-[(2-hydroxyethyl)amino]-2-nitrobenzene (HC Red No. 7), 2-amino-4,6-dinitrophenol, 2-ethylamino-4,6-dinitrophenol, 4-amino-2-nitro-diphenylamine (HC Red No. 1), 1-amino-4-[(di(2-hydroxyethyl)amino]-2-nitrobenzene hydrochloride (HC Red No. 13), 1-amino-5-chloro-4-[(2-hydro-xyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)amino]-3-nitrophenol, 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-methylamino-4-nitrophenol, 2-chloro-6-[(2-hydroxyethyl)amino]-4-nitrophenol, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzoxazine (HC Red No. 14), 1,4-bis[(2-hydroxyethyl)amino]-2-nitrobenzene, 1-(2-hydroxyethyl)amino-2-nitro-4-[di(2-hydroxyethyl)amino]benzene (HC Blue No. 2), 1-amino-3-methyl-4-[(2-hydroxyethyl)amino]-6-nitrobenzene (HC Violet No. 1), 4-[ethyl-(2-hydroxyethyl)amino-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-[(4-amino-2-nitrophenyl)amino]-5-dimethylaminobenzoic acid (HC Blue No. 13), 1,4-di[(2,3-dihydroxypropyl)amino]-9,10-anthraquinone. 1-[(2-hydroxyethyl)amino]-4-methylamino-9,10-anthraquinone (Cl 61505; Disperse Blue No. 3), 2-[(2-aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropyl)amino]-9,10-anthraquinone (HC Red. No. 8), 1,4-diamino-2-methoxy-9,10-anthraquinone (CI 62015, Disperse Red. No. 11, Solvent Violet No. 26), 1,4-dihydroxy-5,8-bis[(2-hydroxyethyl)amino]-9,10-anthraquinone (CI 62500, Disperse Blue No. 7, Solvent Blue No. 69), 1-[di(2-hydroxyethyl)amino]-3-methyl-4-[(4-nitrophenyl)azo]benzene (CI 11210, Disperse Red No. 17), 4-[(4-aminophenyl)azo]-1-[di(2-hydroxyethyl)amino]-3-methylbenzene (HC Yellow No. 7), 2,6-diamino-3-[(pyridin-3-yl)azo]-pyridine and 2-{[4-(acetylamino)phenyl]azo}-4-methylphenol (CI 11855, Disperse Yellow No. 3). Particularly noteworthy in the group of direct dyes are 2-amino-4,6-dinitrophenol, 2-ethylamino-4,6-dinitrophenol, 2-[(2-hydroxyethyl)amino]-4,6-dinitrophenol and dyes of general formula (IX)

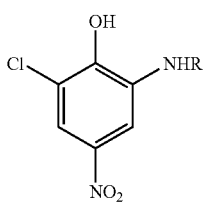

Formula (IX)

wherein R denotes hydrogen, a methyl group, an ethyl group or a hydroxyethyl group.

The total concentration of direct dyes in the agent of the invention is about 0.1 to 10 weight percent and preferably about 0.1 to 5 weight percent.

If the dyes are bases, they can, of course, also be used in the form of their physiologically tolerable salts of organic or inorganic acids, for example hydrochloric acid or sulfuric acid or—if they contain aromatic OH groups—in the form of their salts of bases, for example as alkali metal phenoxides.

For coloring, the afore-described compounds of the invention of formula (I) are applied in an appropriate dye carrier composition—optionally in combination with oxidative hair dye precursors and/or direct dyes.

Moreover, the colorant can contain other common additives, for example antioxidants such as ascorbic acid, thioglycolic acid or sodium sulfite, as well as perfume oils, penetrants, buffer systems, complexing agents, preservatives, wetting agents, emulsifiers, thickeners and hair-care agents.

The colorant of the invention can, for example, be in the form of a solution, particularly an aqueous or aqueous-alcoholic solution. Particularly preferred preparation forms are, however, creams, gels or emulsions. Their composition consists of a mixture of dye components with additives commonly used for such preparations.

Common additives to solution, creams, emulsions or gels are, for example, solvents such as water, the lower aliphatic alcohols, for example ethanol, propanol or isopropanol, glycerol or glycols such as 1,2-propylene glycol, furthermore wetting agents or emulsifiers from the classes of anionic, cationic, amphoteric or nonionic surface-active substances, such as, for example, the fatty alcohol sulfates, ethoxylated fatty alcohol sulfates, alkyl sulfonates, alkylbenzene sulfonates, alkyltrimethylammonium salts, alkylbetaines, ethoxylated fatty alcohols, ethoxylated nonylphenols, fatty alkanolamides and ethoxylated fatty esters, furthermore thickeners such as the higher fatty alcohols, starches or cellulose derivatives, petrolatum, paraffin oil and fatty acids and also hair-care agents such as cationic resins, lanolin derivatives, cholesterol, pantothenic acid and betaine. The said constituents are used in amounts usually employed for such purposes, for example the wetting agents and emulsifiers at a concentration from about 0.1 to 30 weight percent, the thickeners in an amount from about 0.1 to 30 weight percent and the hair-care agents at a concentration from about 0.1 to 5.0 weight percent.

The ready-to-use hair colorants of the invention are prepared just before use by mixing the dye carrier composition with an oxidant.

Suitable oxidants are primarily hydrogen peroxide or the compounds of addition thereof to urea, melamine, sodium borate or sodium carbonate, in the form of a 1 to 12% and preferably 3 to 6% aqueous solution. The weight ratio of hair colorant to oxidant is preferably about 5:1 to 1:3 and particularly 1:1 to 1:2. Higher amounts of oxidant are used primarily with higher dye concentrations in the hair colorant or when more pronounced bleaching of the hair is to be achieved at the same time. In principle, it is also possible to oxidize the dyes with atmospheric oxygen instead of with the afore-said oxidants.

When the dye carrier composition (the pH of which is about 6 to 11.5) is mixed with the oxidant, which in most cases is acidic (pH about 2 to 6.5), the pH of the ready-to-use hair colorant of the invention assumes a value determined by the amount of alkali in the dye carrier composition and by the amount of acid in the oxidant as well as by the mixing ratio. Depending on the composition, the colorant of the invention can be weakly acidic, neutral or alkaline and in the ready-to-use condition have a pH of about 3 to 11 and preferably about 5 to 10. The base used for pH adjustment is preferably ammonia, but an organic amine such as, for example, 2-amino-2-methyl-1-propanol, tris(hydroxymethyl)aminomethane, monoethanolamine or triethanolamine, or an inorganic base such as sodium hydroxide or potassium hydroxide can also be used. The inorganic or organic acid used for pH adjustment is, for example, phosphoric acid, acetic acid, lactic acid, ascorbic acid, citric acid or tartaric acid.

An amount of this mixture sufficient for the hair treatment is then applied to the hair, an amount which depending on the hair fullness is usually about 60 to 200 grams. The mixture is allowed to act on the hair at about 15 to 50° C. and preferably at 30 to 40° C. for about 10 to 45 minutes and preferably for 30 minutes, after which the hair is rinsed with water and dried. Optionally, after this rinsing the hair can be washed with a shampoo and optionally post-rinsed with a weak organic acid, for example citric acid or tartaric acid. The hair is then dried.

The colorants of the invention containing a cationic 4,5-diaminopyrazole of formula (I) produce hair colorations with excellent color stability, particularly in terms of light fastness, wash fastness and abrasion resistance. As regards the coloring properties, depending on the composition of the colorant constituents, the hair colorants of the invention offer a wide range of different color nuances, particularly in the range of the trendy red shades. The color shades obtained are characterized by unusual color intensity and brightness. The very good coloring properties of the colorants according to the present application manifest themselves particularly in that these colorants produce a uniform and lasting coloration also on hair that has previously been damaged to varying degrees.

The compounds of formula (I) can be prepared by the following method:

First, the 4,5-diaminopyrazole derivative is protected against the subsequently used alkylating agent by the introduction of a protective group. To this end, the pyrazole is preferably provided with a protective group that can later be readily removed, particularly by using a t-butoxycarbonyl group as a substituent on the amino group in the 4-position. Advantageous from a preparative standpoint are reactions of pyrazoles with ditert-butyl dicarbonate (BOC anhydride) in the neutral range in a buffered aqueous-organic system, for example water/tetrahydrofuran/sodium hydrogen carbonate. In some cases it may be advantageous to carry out the reaction in two phases, for example in a buffered aqueous solution covered by a layer of an organic phase that is immiscible or only slightly miscible with water. After the introduction of the protective group, the protected pyrazole derivative is extracted from a homogeneous mixture either by use of a water-immiscible solvent or—when the reaction is carried out in a two-phase system—the organic phase is separated and worked up.

The alkylation of the quaternizable nitrogen in the side chain is then carried out in an appropriate solvent. Particularly useful alkylating agents are dialkyl sulfates, aryl sulfonates, alkyl halides and Meerwein salts. Particularly well suited are dimethyl sulfate, dimethyloxonium tetrafluoroborate and diethyloxonium tetrafluoroborate. The reaction temperature depends on the reactivity of the alkylating agent used and ranges from 0 to 160° C. and preferably from 20 to 60° C. Particularly preferred are alkylations with dimethyl sulfate at room temperature (20 to 30° C.). Solvents that are particularly well suited for carrying out the alkylation are ethyl acetate, dioxane, acetone, tetrahydrofuran, acetonitrile, butyronitrile or 3-methoxypropionitrile and a mixture of these solvents. Following the alkylation, the resulting quaternary ammonium salts are separated. Even in the crude state, the ammonium salts are usually quite pure. Without further drying, the BOC protective groups can then be readily removed in an acidic medium.

The acids used for the removal of the protective groups, for example, hydrochloric acid, sulfuric acid, phosphoric acid, citric acid or tartaric acid, at the same time stabilize the directly resulting cationic 4,5-diaminopyrazoles of formula (I). Particularly well suited for this purpose is a mixture of hydrochloric acid and dioxane.

The method will be illustrated by way of Scheme 1 concerning a concrete example [compound of formula (I) with R1=R2=H, L=CH$_2$, Q$^+$=N-methylpyridinium, X$^-$=methylsulfate; corresponds to formula (I-a)].

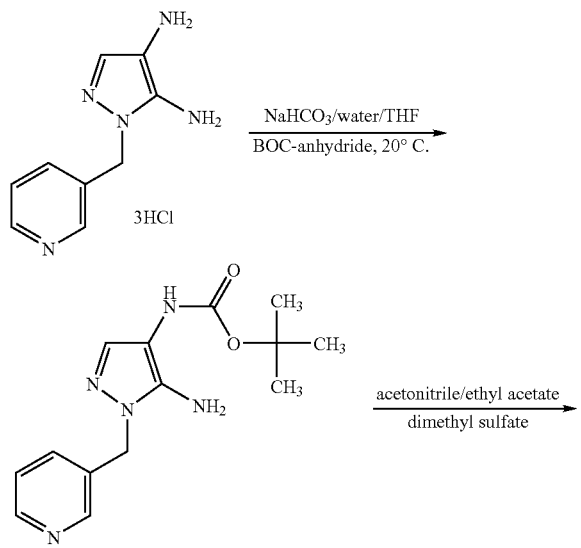

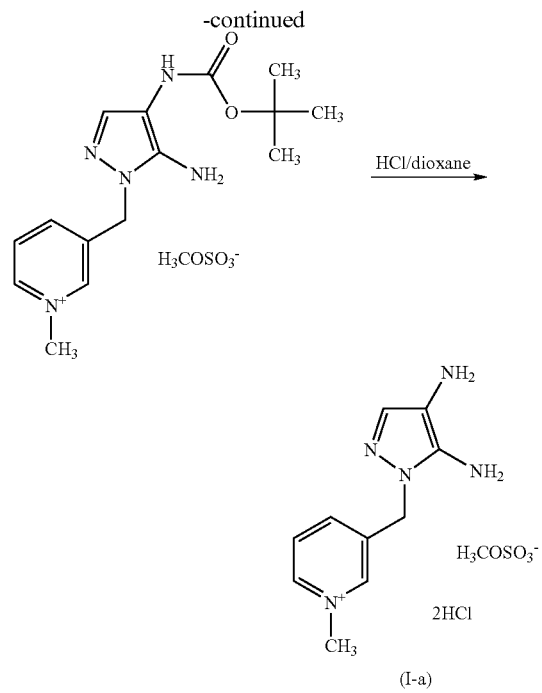

The following examples will explain the subject matter of the invention without limiting it to the examples.

EXAMPLES

Example 1

Preparation of 3-[(4,5-diamino-1H-pyrazol-1-yl)methyl]-1-methylpyridinium Methylsulfate Dihydrochloride Step 1.1: 2-Pyridin-3-ylmethyl-2H-pyrazol-3-ylamine This substance was prepared in 87% yield by a process analogous to that described in FR-A 983 037 or by H. Höhn, Z. Chem., 10$^{th}$ year (1970), vol. 10, by using pyridine-3-carbaldehyde instead of pyridine-4-carbaldehyde.

Melting point: 111-112° C.

$^1$H-NMR (DMSO-d$_6$): δ=8.46 ppm (dd, 1H); 8.40 ppm (d, 1H); 7.50 ppm (m, 1H); 7.35 ppm (dd, 1H); 7.11 ppm (d, 1H); 5.34 ppm (s, 1H); 5.31 ppm (d, 2H); 5.17 ppm (s, 2H).

Elemental analysis:

| [C$_9$H$_{10}$N$_4$; mol. wt. = 174.21] | | | |
|---|---|---|---|
| | % C | % H | % N |
| Calcd.: | 62.05 | 5.79 | 32.16 |
| Found: | 62.01 | 5.88 | 32.46 |

Step 1.2: 4-Nitroso-2-pyridin-3-ylmethyl-2H-pyrazol-3-ylamine 39.2 g (225 mmol) of the substance from Step 1.1 was dissolved in 400 mL of ethanol and 40.5 g of a 32% hydrochloric acid solution and 29 g (248 mmol) of isopentyl nitrite was added to the solution at 0 to 5° C. over a period of 20 minutes. The mixture was allowed to agitate for 3 hours in an ice bath which gave a yellow suspension. The mixture was suction-filtered, and the filter cake was washed with a small amount of ethanol and then dried under vacuum. This gave 42 g of an orange-colored crude product that could be used for the following step without further purification.

Step 1.3: 2-Pyridin-3-ylmethyl-2H-pyrazolyl-3,4-diamine Trihydrochloride 8 g of the crude product from Step 1.2 in 120 mL of ethanol was hydrogenated using 0.8 g of Pd/C (10%) at 9 bar of hydrogen pressure. After 4 hours, the catalyst was filtered off, 20 mL of 32% hydrochloric acid was added to the filtrate and the solution was concentrated under reduced pressure that caused the product to precipitate. The mixture was suction-filtered and the product was recrystallized from 30 mL of ethanol. Drying under vacuum gave 8 g of a colorless product.

$^1$H-NMR (DMSO-d$_6$): δ=10.1 (s, broad, 6H+ water); 8.91 ppm (d, 1H); 8.80 ppm (s, 1H); 8.35 ppm (m, 1H); 8.10 ppm (m, 1H); 7.38 ppm (s, 2H); 5.49 ppm (s, 2H).

Elemental analysis:

| [C$_9$H$_{11}$N$_5$•3 HCl; mol. wt. = 298.6] | | | |
|---|---|---|---|
| % C | % H | % N | % Cl |
| Calcd.: 36.20 | 4.73 | 23.45 | 35.62 |
| Found: 36.30 | 4.70 | 23.40 | 35.40 |

Step 1.4: tert.Butyl-5-amino-1-(3-pyridinylmethyl)-1H-pyrazol-4-yl Carbamate 4 g (18 mmol) of ditert.butyl dicarbonate was added to 4.51 g (15 mmol) of the compound from Step 1.3 in a mixture of 50 mL of tetrahydrofuran and 25 mL of a saturated sodium hydrogen carbonate solution and the mixture was stirred at room temperature for 1 hour. At the end of the reaction, uniform gas evolution was observed. The reaction mixture was then poured into 200 mL of water and the mixture was extracted three times with 350-mL portions of ethyl acetate. The combined organic phases were dried over magnesium sulfate, and the resulting solution was concentrated to about 30 mL which produced a precipitate. The precipitate was suction-filtered, washed with a small amount of ethyl ether and dried under vacuum. This gave 2.8 g (69% of the theoretical) of a colorless solid.

$^1$H-NMR (DMSO-d$_6$): δ=8.46 ppm (d, 1H); 8.39 ppm (s, 1H); 8.18 ppm (s, 1H); 7.51 ppm (d, 1H); 7.34 ppm (m, 1H); 7.20 ppm (s, 1H); 5.14 ppm (s, 2H); 5.00 ppm (s, 2H); 1.43 ppm (s, 9H). Treating the sample with D$_2$O caused the disappearance of the signals at 8.18 and 5.00 ppm.

Step 1.5: tert.Butyl-5-amino-1-[(1-methyl-3-pyridiniumyl)methyl]-1H-pyrazol-4-yl Carbamate Methylsulfate 0.63 g (5 mmol) of dimethyl sulfate was added to 1.45 g (5 mmol) of the compound from Step 1.4 in 15 mL of a 1:1 mixture of ethyl acetate and acetonitrile at room temperature. The mixture was allowed to agitate overnight at room temperature and the precipitate was filtered off and washed with a small amount of ethyl ether. This gave 1.8 g (87% of the theoretical) of a pale-yellow salt melting at 141 to 142° C.

$^1$H-NMR (DMSO-d$_6$): δ=8.91 ppm (d, 1H); 8.87 ppm (s, 1H); 8.27 ppm (s, 1H); 8.19 ppm (d, 1H); 8.10 ppm (t, 1H); 7.31 ppm (s, 1H); 5.32 ppm (s, 2H); 5.08 ppm (s broad, 2H); 5.35 ppm (s, 3H); 3.37 ppm (s, 3H); 1.43 ppm (s, 9H).

Step 1.6 3-[(4,5-Diamino-1H-pyrazol-1-yl)methyl]-1-methylpyridinium Methylsulfate Dihydrochloride At room temperature, 0.5 g (1.2 mmol) of the compound from Step 1.5 was added to 10 mL of a 4-molar solution of hydrochloride in dioxane, and the mixture was stirred for 15 minutes. This gave a colorless suspension. The precipitate was suction-filtered, washed with a small amount of dioxane and dried under vacuum. This gave 1.8 g (93% of the theoretical) of a colorless product which on exposure to air very rapidly assumed a red color.

$^1$H-NMR (DMSO-d$_6$): δ=10.02 ppm (s broad, 2H); 8.99 ppm (s, 1H); 8.96 ppm (d, 1H); 8.27 ppm (d, 1H); 8.13 ppm (dd, 1h); 7.34 ppm (s, 1H); 5.42 ppm (s, 2H); 4.80 ppm (s broad, 2H); 4.36 ppm (s, 3H); 3.57 (s, 9H).

Example 2

Preparation of 4-[(4,5-Diamino-1H-pyrazol-1-yl)methyl]-1-methylpyridinium Methylsulfate Dihydrochloride Step 2.1: 2-Pyridin-4-ylmethyl-2H-pyrazol-3-ylamine The substance was prepared as described in FR-A 983 037 or by H. Höhn, Z. Chem. 10th year (1970), vol. 10.

$^1$H-NMR (DMSO-d$_6$): δ=8.49 ppm (m, 2H); 7.14 ppm (d, 1H); 7.02 ppm (d, 1H); 5.34 ppm (m, 3H); 5.18 ppm (s, 2H).

Step 2.2: 4-Nitroso-2-pyridin-4-ylmethyl-2H-pyrazol-3-ylamine Hydrochloride 30 g (172 mmol) of the compound from Step 2.1 was suspended in 300 mL of ethanol and 1 g of 32% hydrochloric acid solution and to the suspension was added dropwise, in an ice bath, 22.1 g (189 mmol) of isopentyl nitrite over a period of 10 minutes. The mixture was allowed to agitate in the ice bath for an additional 3 hours, which gave a brownish suspension. The mixture was then filtered, and the filter cake was washed with a small amount of cold ethanol and dried. This gave 38.1 g (92% of the theoretical) of an orange-colored solid that could be used in the next step without further purification.

Step 2.3: 2-Pyridin-4-ylmethyl-2H-pyrazole-3,4-diamine Trihydrochloride

In an autoclave, 38.1 g (158 mmol) of the crude product from Step 2.2 was suspended in 800 mL of ethanol and hydrogenated at 9 bar of hydrogen pressure for 2 hours using 3.8 g of Pd/C (10%). The catalyst was then filtered off through diatomaceous earth, to the filtrate was added 200 mL of 3M ethanolic hydrochloric acid, and the solution was concentrated to incipient crystallization in a rotary evaporator at 40° C. To complete the crystallization, the mixture was cooled in an ice bath, after which the solid was filtered off. The product was then washed with a small amount of ethyl acetate and dried at 40° C. under vacuum. This gave 19.5 g (41% of the theoretical) of a slightly pink-colored powder.

$^1$H-NMR (DMSO-d$_6$): δ=10.2 ppm (s broad, 3H); 8.92 ppm (d, 2H); 7.66 ppm (d, 2H); 7.41 ppm (s, 1H); 7.20 ppm (s broad, 3H+ water); 5.62 ppm (s, 2H).

Elemental analysis:

| [C$_9$H$_{11}$N$_5$(2.86HCl)/0.38H$_2$O)] | | | |
|---|---|---|---|
| % C | % H | % N | % Cl |
| Calcd.: 35.99 | 4.91 | 23.32 | 35.76 |
| Found: 35.80 | 4.80 | 23.30 | 33.80 |

Step 2.4: t-Butyl-5-amino-1-(4-pyridinylmethyl)-1H-pyrazol-4-yl Carbamate 1.4 g (4.7 mmol) of the product from Step 2.3 was suspended in 30 mL of tetrahydrofuran and to the mixture was added 12 mL of saturated sodium hydrogen carbonate solution which caused slight gas evolution and gave a brownish solution. 2.05 g (9.4 mmol) of BOC anhydride was added, and the mixture was allowed to agitate 2 hours at room temperature. The reaction mixture was then poured into 100 mL of water and extracted twice with 100-mL portions of ethyl acetate. The combined phases were dried over magnesium sulfate, and the solution was then evaporated to incipient crystallization in a rotary evaporator. After agitation in an ice bath, filtration and washing of the filter cake with a small amount of cold ethyl acetate, the product was dried at 40° C. under vacuum. This gave 0.8 g (59% of the theoretical) of a beige-colored product.

$^1$H-NMR (DMSO-d$_6$): δ=8.49 ppm (d, 2H); 8.21 ppm (s, 1H); 7.24 ppm (s, 1H); 7.02 ppm (d, 2H); 5.15 ppm (s, 2H); 4.98 ppm (s, 2H); 1.44 ppm (s, 9H).

Step 2.5: t-Butyl-5-amino-1-[(1-methyl-4-pyridiniumyl)methyl]-1H-pyrazol-4-yl Carbamate Methylsulfate 0.38 g (3 mmol) of dimethyl sulfate was added to 0.69 g (2.4 mmol) of the product from Step 2.4 in 10 mL of ethyl acetate, and the mixture was allowed to agitate overnight. A viscous oil separated. The supernatant solution was decanted and discarded. The residue was used in the next step without further purification.

Step 2.6: 4-[(4,5-Diamino-1H-pyrazol-1-yl)methyl]-1-methylpyridinium Methylsulfate Dihydrochloride 10 mL of 4M hydrochloric acid in dioxane was added to the residue from Step 2.5 and the mixture was stirred 1 hour at room temperature. The resulting crystalline precipitate was suction-filtered, washed with a small amount of dioxane and dried at 40° C. under vacuum. This gave 100 mg of a slightly pink-colored, very hygroscopic product.

$^1$H-NMR (DMSO-d$_6$): δ=10.09 ppm (s broad, 2H); 8.94 ppm (d, 1H); 8.88 ppm (d, 1H); 7.68 ppm (d, 1H); 7.61 ppm (d, 1H); 7.38 ppm (s, 1H); 5.55 ppm (s, 2H); 4.31 ppm (s, 3H); 5.57 ppm (s, 3H).

Example 3

| Oxidation Hair Colorant, Basic | |
|---|---|
| 0.30 g | of ascorbic acid |
| 0.40 g | of sodium sulfite |
| 2.00 g | of decyl glucoside |
| 7.85 g | of ethanol |
| 0.97 g | of pyrazole of formula (I) from Example 1.6 |
| Z g | of coupler as per Table 1 |
| 9.10 g | of ammonia, 25% aqueous solution |
| to 100.00 g | water, demineralized |

Just before use, 100 grams of the foregoing dye carrier composition was mixed with 100 g of a 6% aqueous hydrogen peroxide solution, and the required amount of the resulting ready-to-use colorant solution was applied to bleached hair. After an exposure time of 30 minutes at 40° C., the hair was washed with a shampoo, rinsed with water and dried. The color nuances and color intensities obtained are summarized in Table 1.

TABLE 1

| Example | Coupler, g | Shade | Intensity |
|---|---|---|---|
| 3a | 3-aminophenol, 0.27 g | chimney red | ++ |
| 3b | resorcinol, 0.28 g | pink | o |
| 3c | 5-amino-2-methylphenol, 0.31 g | bright orange-red | ++ |
| 3d | 1,3-diamino-4-(2-hydroxy-ethoxy)benzenene dihydrochloride, 0.60 g | dark-violet | ++ |
| 3e | 3-dimethylaminophenylurea, 0.45 g | steel-blue | ++ |

(o) = medium,
(+) = strong,
(++) = very strong

Unless otherwise indicated, all percentages given are by weight.

The invention claimed is:

1. An agent for the oxidative coloring of keratin fibers, comprising at least one cationic 4,5-diaminopyrazole derivative selected from the group consisting of:
   3-[(4,5-diamino-1H-pyrazol-1-yl)methyl]-1-methylpyridinium methylsulfate dihydrochloride,
   4-[(4,5-diamino-1H-pyrazol-1-yl)methyl]-1-methylpyridinium methylsulfate dihydrochloride,
   2-[(4,5-diamino-1H-pyrazol-1-yl)methyl]-1-methylpyridinium methylsulfate dihydrochloride,
   4-[(4,5-diamino-1H-pyrazol-1-yl)methyl]-1-methylpyridinium methylsulfate dihydrochloride,
   3-[(4,5-diamino-1H-pyrazol-1-yl)methyl]-1-methylpyridinium methylsulfate dihydrochloride,
   4-[2-(4,5-diamino-1H-pyrazol-1-yl)ethyl]-1-methylpyridinium methylsulfate dihydrochloride,
   1-[2-(4,5-diamino-1H-pyrazol-1-yl)ethyl]-1-methylpyrrolidinium chloride dihydrochioride,
   4-[2-(4,5-diamino-1H-pyrazol-1-yl)ethyl]-4-methylmorpholin-4-ium chloride dihydrochloride and
   3-[2-(4,5-diamino-1H-pyrazol-1-yl)ethyl]-1-methyl-1H-imidazol-3-ium chloride dihydrochloride.

2. An agent as defined in claim 1, wherein the cationic 4,5-diamino-pyrazole derivative is present in an amount from 0.005 to 20 weight percent.

3. An agent as defined in claim 1, and further comprising at least one other developer and/or coupler and/or at least one direct anionic, cationic, amphoteric or nonionic dye.

4. An agent as defined in claim 1, wherein the agent has a pH of 3 to 11.

5. An agent as defined in claim 1, wherein the agent is mixed with an oxidant before use.

6. An agent as defined in claim 1, wherein the agent is a hair colorant.

* * * * *